United States Patent [19]

Yoshimura et al.

[11] 4,356,333
[45] Oct. 26, 1982

[54] PROCESS FOR PREPARING N-OCTADIENOL

[75] Inventors: Noriaki Yoshimura; Masuhiko Tamura, both of Kurashiki, Japan

[73] Assignee: Kuraray Company, Limited, Kurashiki, Japan

[21] Appl. No.: 247,290

[22] Filed: Mar. 25, 1981

[30] Foreign Application Priority Data

Mar. 28, 1980 [JP] Japan ............................ 55-40989
Apr. 11, 1980 [JP] Japan ............................ 55-48256
Jan. 26, 1981 [JP] Japan ............................ 56-10560

[51] Int. Cl.³ ............................................. C07C 29/00
[52] U.S. Cl. .................................. 568/840; 252/431 P
[58] Field of Search ........................................ 568/840

[56] References Cited

U.S. PATENT DOCUMENTS

| | | | |
|---|---|---|---|
| 3,407,224 | 10/1968 | Smutny | 568/840 X |
| 3,670,032 | 6/1972 | Romanelli | 568/840 X |
| 3,887,627 | 6/1975 | Romanelli | 568/840 |
| 4,142,060 | 2/1979 | Kuntz | 568/840 |

*Primary Examiner*—Bernard Helfin
*Attorney, Agent, or Firm*—Oblon, Fisher, Spivak, McClelland & Maier

[57] ABSTRACT

A process for preparing n-octadienol comprising the steps of:
(i) reacting butadiene with water in an aqueous sulfolane solution having a water/sulfolane weight ratio in the range of 20/80 to 70/30 and containing carbonate and/or bicarbonate ions in the presence of (A) palladium or a palladium compound, (B) a monodentate phosphine of the formula:

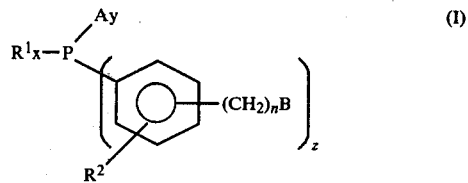

[wherein $R^1$ is an aliphatic, alicyclic or substituted or unsubstituted aromatic hydrocarbon group having 1 to 8 carbon atoms; $R^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that $x+y+z=3$;

A is $-CH_2\overset{\underset{\displaystyle |}{CH_3}}{C}HCOOM$, $-C(CH_3)_2COOM$, $-CH_2\overset{\underset{\displaystyle |}{CH_3}}{C}HN\overset{R^3}{\underset{R^{4'}}{<}}$, $-C(CH_3)_2N\overset{R^3}{\underset{R^{4'}}{<}}$, a carbonate or bicarbonate of 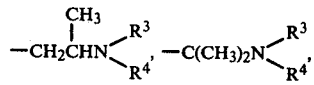

or a carbonate or bicarbonate of $-C(CH_3)_2N\overset{R^3}{\underset{R^{4'}}{<}}$, and B is $-SO_3M$, $-COOM$, $-N\overset{R^3}{\underset{R^4}{<}}$ or a carbonate or bicarbonate of $-N\overset{R^3}{\underset{R^4}{<}}$, wherein $R^3$ and $R^4$ are each methyl, ethyl or n-propyl and M is an alkali metal]

in an amount of at least 6 moles per gram atom of the palladium and (C) a monodentate tertiary amine having a basicity constant (pKa) of 7 or more in an amount of 1 to 50% by volume based on the sulfolane to form n-octadienol;
(ii) subjecting at least part of the reaction mixture obtained in step (i) to extraction with a saturated aliphatic hydrocarbon, a monoolefinic hydrocarbon or an alicyclic hydrocarbon; and
(iii) recycling at least part of the extraction residue obtained in step (ii) which contains the catalyst components to step (i).

22 Claims, No Drawings

PROCESS FOR PREPARING N-OCTADIENOL

This invention relates to an improved process for preparing n-octadienol by the reaction of butadiene and water. n-Octadienol is useful as an intermediate for synthetic resin modifiers, agricultural chemicals, medicines, perfumes, and the like. Particularly, n-octanol which is obtained by reduction of n-octadienol is an important starting material for the preparation of di-n-octyl phthalate which is widely used as a plasticizer for polyvinyl chloride and similar polymers. Di-n-octyl phthalate is superior in use in various basic applications in comparison to the commonly used dioctyl phthalate derived from 2-ethylhexanol. Nevertheless, di-n-octyl phthalate has not yet been used in large quantities as a plasticizer, since there is no established commercial process for preparing its starting material, i.e., n-octanol inexpensively.

Under these circumstances, it has been proposed that n-octanol can be prepared by reacting butadiene with water in the presence of a palladium catalyst to synthesize n-octadienol followed by hydrogenation of n-octadienol (e.g., U.S. Pat. No. 3,670,032). However, according to the process disclosed in U.S. Pat. No. 3,670,032, both the rate of formation of n-octadienol and the selectivity toward it are extremely low so that the process is not suitable for the commercial production of n-octanol. It is already known that the rate of formation of octadienol can be increased by adding carbon dioxide to the above reaction system (British Pat. No. 1,307,101, J.Chem Soc., Chem. Commun., 330 (1971), etc.). However, as can be seen from the description in Chem. Commun., 330 (1971), the process described in these articles suffers from a disadvantage which can be said to be fatal in that, when the amount of a phosphine added as a ligand to maintain the catalyst life exceeds 5 moles per gram atom of the palladium, the reaction rate and selectivity are sharply decreased. Since palladium is an extremely expensive metal, it is essential for the commercial production of n-octadienol by the reaction of butadiene with water to keep the activity of the catalyst stable for a prolonged period of time. In order to stabilize the activity of the catalyst, an addition of the phosphine in excess is necessary, but such excessive addition of the phosphine leads to unsatisfactory results in that, as mentioned above, both the rate of formation of and the selectivity toward n-octadienol are decreased. Furthermore, in the processes for the synthesis of n-octadienol which have heretofore been proposed, n-octadienol is generally isolated by direct distillation from the reaction mixture, and the distillation residue containing the catalyst components is recycled to the reaction system. However, according to our detailed study and as suggested in U.S. Pat. No. 3,670,032, it is noted that the palladium catalyst has a tendency toward deterioration or metallization at distillation temperatures exceeding about 120° C. The deterioration and metallization of the palladium catalyst are serious problems from a commercial point of view, since these factors not only result in a decrease in the catalyst activity, but they make substantially impossible a continuous, reuse of the catalyst. In order to suppress the deterioration and metallization of the palladium catalyst, it is necessary to conduct the distillation of products from the reaction mixture at a temperature of 120° C. or below, but in such cases other problems such as a build-up of high boiling by-products including octadienyl ether in the reaction system and a decrease in the distillation yield of n-octadienol may arise.

Another method for the isolation of the octadienol which does not resort to direct distillation of the reaction mixture is suggested in U.S. Pat. No. 4,142,060, wherein n-octadienol synthesis is conducted in a water solvent. In this case the product can be easily separated from the reaction mixture since the catalyst is dissolved mainly in the water solvent. However, this method has a serious disadvantage in that the reaction rate is extremely low because of the very poor solubility of butadiene in water and because the selectivity toward n-octadienol is also low. Moreover, when the reaction is carried out in the mixture of the organic solvent and water as described in U.S. Pat. No. 4,142,060 in order to improve the reaction rate, either the reaction mixture forms a homogeneous system in which it is impossible to separate n-octadienol from the catalyst, or in the event the reaction mixture forms a heterogeneous system reuse of the palladium catalyst is substantially impractical since large amounts of the palladium catalyst and solvent are transferred to the octadienol layer. In addition, as previously mentioned, when the phosphine is added in large excess relative to the palladium in order to stabilize the palladium catalyst, both the rate and the selectivity of the reaction sharply decrease. This problem is not solved by any way in the process proposed in U.S. Pat. No. 4,142,060, too.

Thus, in order to achieve a truly industrial valuable method of n-octadienol synthesis by the reaction of butadiene and water in the presence of the palladium catalyst, it is essential to solve several problems which include the following: (1) The rate and the selectivity of the reaction must be improved to commercially acceptable levels, (2) Catalyst life must be maintained over a prolonged period of time. (3) The product must be isolated from the reaction mixture and the catalyst must be recycled without loss in the catalyst activity.

From these points of view, a detailed study of the synthesis of n-octadienol by the reaction of butadiene and water in the presence of the palladium catalyst has been conducted and it has been found that the various problems mentioned above can be solved by a process which comprises conducting the reaction of butadiene and water in an aqueous sulfolane solution having a water/sulfolane weight ratio of 20/80 to 70/30 in the presence of a monodentate phosphine ligand having a particular structure, subjecting the reaction mixture to solvent extraction, and recycling the extraction residue containing the catalyst components to the first step, i.e., the reaction of butadiene and water.

Thus, the process of the present invention comprises the steps of:

(i) reacting butadiene with water in an aqueous sulfolane solution having a water/sulfolane weight ratio in the range of 20/80 to 70/30 and containing carbonate and/or bicarbonate ions in the presence of (A) palladium or a palladium compound, (B) a monodentate phosphine of the formula:

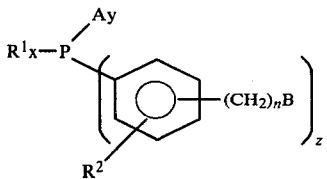

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that $x+y+z=3$;

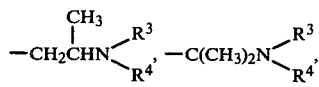

and B is $-SO_3M$, $-COOM$, $-N\begin{smallmatrix}R^3\\R^4\end{smallmatrix}$ or a carbonate or bicarbonate of $-N\begin{smallmatrix}R^3\\R^4\end{smallmatrix}$, wherein $R^3$ and $R^4$ are each methyl, ethyl or n-propyl and M is an alkali metal in an amount of at least 6 moles per gram atom of palladium and (C) a monodentate tertiary amine having a basicity constant (pKa) of 7 or more in an amount of 1 to 50% by volume based on the sulfolane to form n-octadienol;

(ii) subjecting at least part of the reaction mixture obtained in step (i) to extraction with a saturated aliphatic hydrocarbon, a monoolefinic hydrocarbon or an alicyclic hydrocarbon; and (iii) recycling at least part of the extraction residue obtained in step (ii) which contains the catalyst components to step (i).

According to the process of the present invention, n-octadienol is produced at a high rate and at high selectivity even if the phosphine is added in large excess relative to the palladium. Moreover the catalytic activity can be kept stable over a prolonged period of time, since the phosphine can be added in large excess relative to the palladium. Also in accordance with the present process, not only n-octadienol can be separated very easily and efficiently from the reaction mixture, but the dissolution of the palladium and phosphine into the extractant layer which is a significant industrial problem in the extraction step is suppressed to a very low level. In addition, in accordance with the present process, the catalyst can be reused by recycling the extraction residue obtained in the extraction step which contains the catalyst components to the n-octadienol synthesis step, and hence the preparation of n-octadienol by the reaction of butadiene and water can be conducted, as a whole, in a commercially advantageous fashion.

It has been found that in the reaction of Step (i) of the present process the use of an aqueous sulfolane solution having a water/sulfolane weight ratio of 20/80 to 70/30 as a reaction medium and of a monodentate phosphine having the particular structure shown as a ligand offers many advantages as are described below in the n-octadienol synthesis, in contrast with the use of other reaction media used in the prior-art synthesis of n-octadienol such as aqueous t-butanol, tetrahydrofuran, acetone, dioxane, N-methylpyrrolidone, acetonitrile, dimethyl sulfoxide and dimethylformamide solution, and the like or the use of water alone.

(1) By carrying out the reaction in an aqueous sulfolane solution containing a monodentate tertiary amine having a basicity constant (pKa) of 7 or more, the reaction rate can be significantly increased with the selectivity toward n-octadienol being maintained at a high level of 90% or above. In contrast, if any other reaction medium is used, the addition of the tertiary amine cannot bring about any acceleration of the reaction. For example, as indicated in Table 7 of British Pat. No. 1,307,101, the addition of triethylamine (pKa=10.67) to such a reaction system results in a significant decrease in the reaction rate and selectivity.

(2) In the reaction in an aqueous sulfolane solution, even if the phosphine is added in large excess on the order of 10 moles or more per gram atom of the palladium, the degree of decrease in the reaction rate is very slight and n-octadienol can be obtained with a high selectivity of at least 90%. On the other hand, if other reaction media are used, as is apparent from J. Chem. Soc., Chem. Commun., 330 (1971) and British Pat. No. 1,307,101 (Table 5), the addition of the phosphine ligand to the reaction system in such an amount as required to keep the activity of the palladium catalyst stable brings about not only a decrease in the reaction rate, but an increase in the proportion of 3-octadienol (a secondary alcohol) formed as a by-product. Consequently the selectivity of n-octadienol is about 75% or less.

(3) In accordance with the process of the present invention, when the reaction is conducted in an aqueous sulfolane solution containing a large proportion of water, the reaction mixture forms a heterogeneous system under which reaction conditions butadiene separates from the other components. Nevertheless, the desired n-octadienol is produced at a satisfactorily high rate of formation. Such reaction in a heterogeneous condition permits an easy extraction of the product from the reaction mixture. It is suggested in U.S. Pat. No. 3,670,032 and British Pat. No. 1,307,101 that, since in the reaction in a heterogeneous system the palladium catalyst and butadiene are preferentially dissolved in the organic layer whereby the reaction rate is significantly decreased, a small amount of water should be used together with organic solvent in such amount as required to keep the reaction mixture homogeneous. In this case, however, the product must subsequently be isolated by direct distillation of the reaction mixture containing the catalyst, and such distillation brings about a decrease in catalyst activity.

(4) Sulfolane has a markedly good chemical stability even in an aqueous solution containing a basic compound in comparison to other strong polar solvents, and withstands continuous use for a prolonged period of time.

The aqueous sulfolane solution not only offers the advantages described in (1) to (4) above, but permits easy separation of the product from the reaction mixture by means of extraction. Thus by the combined use of an aqueous sulfolane solution and a monodentate phosphine of formula (I) the palladium catalyst and sulfolane become substantially insoluble in the extractant and losses of the palladium catalyst, phosphine, tertiary amine and sulfolane because of their dissolution into the extractant layer become negligibly small.

Since the problem of deterioration and metallization of the palladium catalyst because of heat and build-up of high boiling by-products can be solved by the adoption of an extraction method, the catalyst activity can be kept more stable. Such advantages attributable to the extraction method can not be obtained in the absence of either the aqueous sulfolane solution or the monodentate phosphine of formula (I). Thus, in cases where the reaction and the subsequent extraction are carried out using, for example, the solvent discribed in U.S. Pat. No. 4,142,060 in place of the aqueous sulfolane solution in step (i), the mutual solubility of the solvent and the extractant is so large that loss of the solvent due to dissolution into the extractant layer is increased, which accompanies increased losses of the palladium and phosphine. Therefore, the extraction procedure cannot be successfully applied to these types of systems. Also in cases where the ligand is triphenylphosphine which is most generally used in the prior art processes, substantial portions of the palladium and phosphine are extracted into the extractant layer even if the n-octadienol synthesis is carried out in an aqueous sulfolane solution, and hence the extraction procedure cannot be successfully applied.

Any palladium or palladium compounds which have heretofore been proposed for use in the synthesis of n-octadienol can be used as the catalyst in the process of the present invention. Palladium in an active form may be supported on a carrier of low activity such as active charcoal. Examples of suitable palladium compounds include palladium acetylacetonate, π-allyl palladium acetate, π-allyl palladium chloride, palladium acetate, palladium propionate, palladium carbonate, palladium nitrate, palladium sulfate, palladium chloride, sodium chloropalladate, potassium chloropalladate, dichlorobis(benzonitrile)palladium, bis(1,5-cyclooctadiene)palladium, bis-π-allyl palladium, 1,5-cyclooctadiene palladium chloride, and the like. The true catalytically active species are palladium complexes of low valency. Therefore, when a divalent palladium compound is used as the catalyst, it may be reduced with the phosphine or butadiene existing in the reaction system to form an active species, or alternatively the catalytically active species may be formed in the presence of a compound having a reducing ability either in the same reaction system or in another reaction vessel. The reducing agents useful for this purpose include alkali metal hydroxides, sodium borohydride, zinc powder, magnesium, hydrazine, alkali metal alkoxides, alkali metal carbonates, and the like. It is practical to use the reducing agents in an approximately stoichiometric amount required to change the valence of palladium. The amount of palladium or palladium compound used is not critical, but from the standpoint of commercial operation, palladium or a palladium compound is desirably used at a concentration of 0.1 to 50 milligram atom, preferably 0.5 to 20 milligram atom as palladium atom per liter of the aqueous sulfolane solution.

In the monodenate phosphines of formula (I), $R^1$ is a hydrocarbon group of 1 to 8 carbon atoms, more specifically an aliphatic hydrocarbon group such as methyl, ethyl, n-propyl, isopropyl, n-butyl, t-butyl, n-octyl or the like; an alicyclic hydrocarbon group such as cyclohexyl, methylcyclohexyl or the like or an aromatic hydrocarbon group such as phenyl, benzyl, tolyl or the like. The aromatic hydrocarbon group may be substituted by a methoxy, chloro, cyano or nitro group. The phosphine of formula (I) in which B is $-SO_3M$ or $-COOM$ is usually used as an alkali metal salt, which is preferably the sodium, potassium or lithium salt. Alternatively, the alkali metal salt may be replaced by the free sulfonic or carboxylic acid or its ester, which is reacted in the reaction system or another reaction vessel with an alkali metal hydroxide, bicarbonate, carbonate or the like to form the alkali metal salt.

Of the monodentate phosphine of formula (I), particularly preferred are di- or triaryl phosphine in which $R^1$ is an aromatic hydrocarbon group, n is 0 or 1, x is 0, 1 or 2, y is 0 or 1, z is 0, 1, 2 or 3 (with the proviso that y and z are not concurrently equal to 0 and that x+y+z=3),

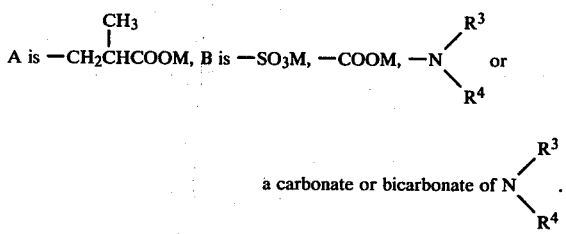

Illustrative of the monodentate phosphines are:

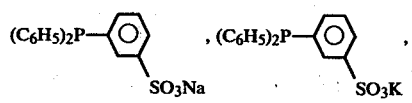

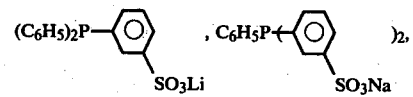

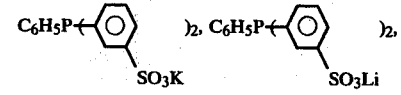

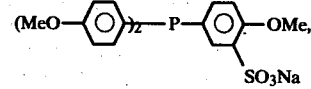

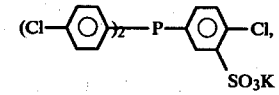

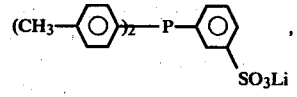

-continued

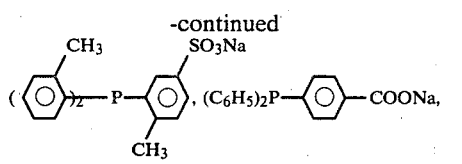

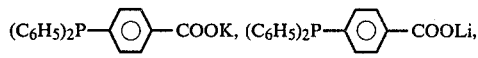

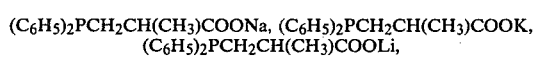

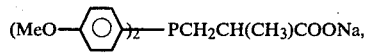

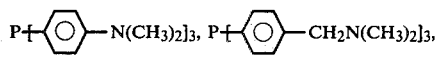

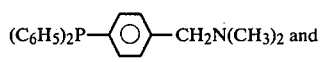

Examples of particularly preferred phosphines are:

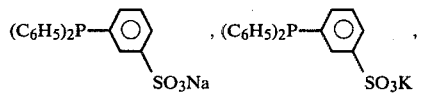

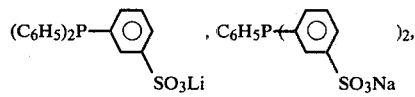

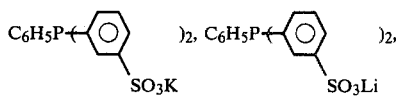

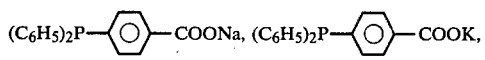

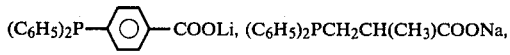

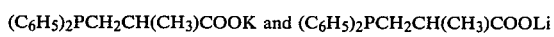

An amino-containing phosphine is usually added to the reaction system as it is. Alternatively, since an amino phosphine is present in the form of its carbonate or bicarbonate salt in the reaction system, a carbonate or bicarbonate of an amino-containing phosphine may be previously prepared and added to the reaction system. The phosphines may be used either singly or in a combination of two or more thereof. The monodentate phosphine should be used in an amount of at least 6 moles, preferably at least 10 moles per gram atom of the palladium. There is no upper limit in a strict sense in the amount of the phosphine, but it is generally desirable that the phosphine is used in an amount of not more than 150 moles, preferably not more than 50 moles per gram atom of the palladium.

According to the findings of the present invention, the monodentate phosphines of formula (I) tend to oxidize into the corresponding phosphine oxides with oxygen exsisting in the reaction system in trace amounts and thereby lose their activities. It has been found that such oxidation of the monodentate phosphines of formula (I) can be inhibited by adding, in combination with such a phosphine, a bidentate phosphine of the formula:

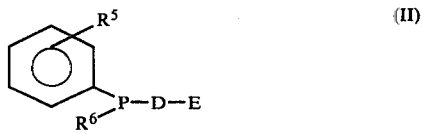

wherein $R^5$ is hydrogen, methyl, halogen, cyano, methoxy, nitro,

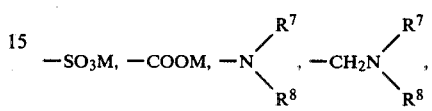

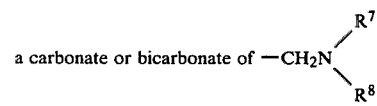

where $R^7$ and $R^8$ are each methyl, ethyl or n-propyl and M is an alkali metal, $R^6$ is a hydrocarbon group having 1 to 8 carbon atoms;

D is $-(CH_2)_n-$ wherein n is an integer of 1 to 4,

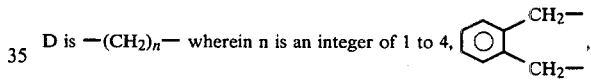

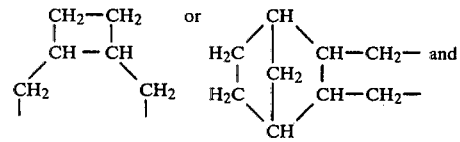

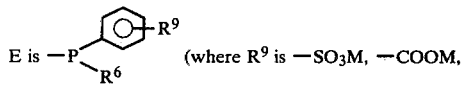

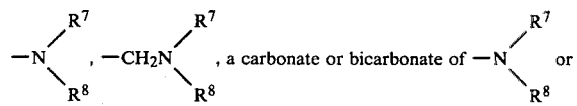

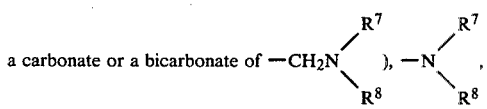

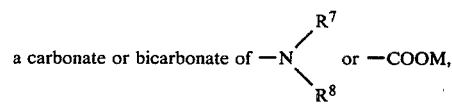

in an amount of 0.3 to 3 moles per gram atom of the palladium. In addition, the use of such a bidentate phosphine permits the palladium catalyst to have an increased thermal stability, which results in stabilization of catalyst activity for a prolonged period. Such an effect is not substantially developed when the amount of the bidentate phosphine is less than 0.3 mole per gram atom of the palladium. In an amount exceeding 3 moles per gram atom of the palladium, the bidentate phosphine causes a marked decrease in the reaction rate.

In the foregoing formula (II), the symbol M in —$SO_3M$ and —COOM in $R^5$, E or $R^9$ represents an alkali metal, which is preferably sodium, potassium or lithium. The hydrocarbon groups having 1 to 8 carbon atoms as $R^6$ include aliphatic hydrocarbon groups such as methyl, ethyl, n-propyl, isopropyl, n-butyl, t-butyl, n-octyl, and the like; alicyclic hydrocarbon groups such as cyclohexyl, and the like; and aromatic hydrocarbon groups such as phenyl, benzyl, tolyl, etc. Of these phenyl is most preferred. Examples of the bidentate phosphines are:

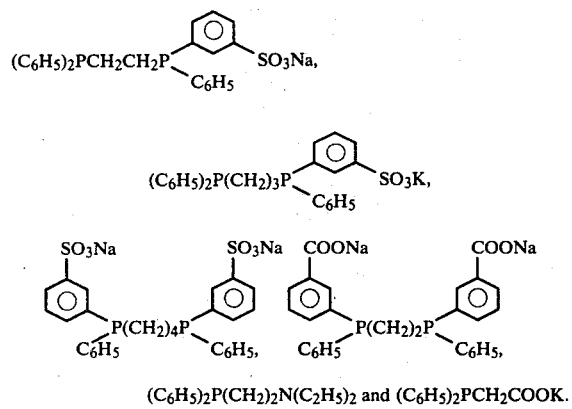

$(C_6H_5)_2P(CH_2)_2N(C_2H_5)_2$ and $(C_6H_5)_2PCH_2COOK$.

The bidentate phosphines may be used either singly or in a combination of two or more.

The amines to be added to the reaction system of this invention are monodentate tertiary amines having a basicity constant (pKa) of at least 7, and the addition of such amines can result in a significant increase in the reaction rate without decrease in the selectivity. This phenomenon is quite unexpected and surprising in view of the fact known in the art that the rate of n-octadienol formation and the selectivity toward n-octadienol significantly decrease upon the addition of even a small amount of triethylamine (pKa 10.67) as reported in Table 7 (Run Nos. 11 and 17) of British Pat. No. 1,307,101.

Such an effect of amine addition on the acceleration of the reaction rate cannot be attained by a mono- or bidentate tertiary amine having a pKa value of less than 7 such as pyridine or α,α'-dipyridyl or by a strong bidentate tertiary amine such as N,N,N',N'-tetramethyldiaminoethane or N,N-dimethyl-2-aminopropionitrile even though such an bidentate amine has a pKa value of 7 or higher.

The monodentate tertiary amines useful in the present invention include tri(lower)alkylamines such as trimethylamine, triethylamine, tri-n-propylamine, tri-n-butylamine, etc.; aminoalcohols such as 1-N,N-dimethylamino-2-propanol, 1-N,N-dimethylamino-3-butanol, etc.; and N,N-dimethyl-2-methoxyethylamine, N,N-dimethyl-3-ethoxypropylamine, N-methylpyrrolidine, N-methylpiperidine, N-methylmorpholine, N,N'-dimethylpiperazine, N,N,N',N'-tetramethyl-1,3-butanediamine and the like. Among these, triethylamine is most preferred in view of various factors including reaction yield, boiling point, solubility and cost. The tertiary amine is generally added in an amount of 1 to 50% by volume based on the sulfolane.

In accordance with the process of this invention, carbonate and/or bicarbonate ions are present along with the tertiary amine to accelerate the rate of n-octadienol formation. Carbonate and bicarbonate ions are conveniently derived from carbon dioxide, sodium bicarbonate or formic acid which releases these ions in the reaction system. Among these, carbon dioxide is most preferred. In the reaction system carbonate and bicarbonate ions react with the tertiary amine to form a carbonate and/or bicarbonate of the amine according to the following equilibrium equation:

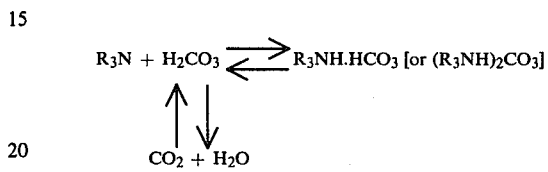

Accordingly, the tertiary amine prior to reaction be reacted with carbonate and/or bicarbonate ions to form the carbonate and/or bicarbonate salt of the amine, which is then added to the reaction system. In view of reaction yield, extraction efficiency, amount of the tertiary amine dissolved into the extract layer, etc., the carbonate and/or bicarbonate of the tertiary amine should be present in the reaction system in an amount of 2 to 30%, preferably 5 to 20% by weight of the reaction mixture. The proportion of the carbonate and/or bicarbonate of the tertiary amine present under the reaction conditions will depend on the temperature and the absolute partial pressure of carbon dioxide in the system. Therefore, the reaction is usually carried out under pressure so as to maintain the absolute partial pressure of carbon dioxide at about 1 to 10 kg/cm². The carbonate and/or bicarbonate ions are not consumed as n-octadienol is formed.

Any commercially available butadiene, for example, a polymerization grade or chemical reaction grade butadiene or a hydrocarbon mixture usually called "C₄-fraction", may be used. Preferably a polymerization grade or chemical reaction grade butadiene is used in view of reaction rate and ease in recovery of unreacted butadiene considerations. The amount of butadiene employed is not critical, but there is a limit to the solubility of butadiene in aqueous sulfolane solutions so that excess butadiene will exist in two different phases in the reaction system. For this reason, the reaction is usually carried out with butadiene being continuously or intermittently introduced into the reaction system so as to maintain the concentration of butadiene in the reaction mixture at 0.1 to 10%, preferably at 1 to 5% by weight.

The aqueous sulfolane solution in the process of the present invention has a water/sulfolane weight ratio in the range of 20/80 to 70/30, preferably in the range of 25/75 to 60/40. When the concentration of the sulfolane is within the above range, the reaction mixture forms a heterogeneous system in which a part of the butadiene is separated from the reaction medium, provided that the concentration of butadiene is within a normal range. By use of an aqueous sulfolane solution with the concentration in the above-mentioned range, n-octadienol can be extracted with high extraction yield and with minimized dissolution of the palladium and phosphine into the extract layer in the subsequent extraction step

[step (ii)], and the rate and selectivity of the reaction are maintained at high levels. Sulfolane concentrations of less than 30% by weight result in a significant decrease in the reaction rate, while at sulfolane concentration exceeding 80% by weight, not only is the extraction efficiency decreased and the amounts of palladium and phosphine dissolved into the extract layer increased, but the amounts of by-products also increase. Water is present in the reaction system as an aqueous sulfolane solution, and it is desirable in view of the solubility of butadiene in aqueous sulfolane solution and the extraction efficiency of n-octadienol that the amount of water in the reaction system be kept at 25 to 60%, preferably 30 to 50% by weight of the reaction mixture. Since water is consumed as n-octadienol is formed, the reaction may be continued with continuous or intermittent addition of the required amounts of water. In such cases, water may be added to the system in any of steps (i), (ii) and (iii).

The n-octadienol synthesis according to the process of this invention is most preferably carried out under the conditions which meet all of the following requirements (1) to (5), since it has been found that under such reaction conditions the rate and selectivity of the reaction in step (i) as well as the extraction efficiency and dissolution loss of the catalyst components in step (ii) are well balanced within satisfactory levels.

(1) The concentration of the palladium or palladium compound is in the range of 0.5 to 20 milligram as palladium atom per liter of the aqueous sulfolane solution.

(2) The phosphine of formula (I) is used in an amount of 10 to 50 moles per gram atom of the palladium.

(3) The carbonate and/or bicarbonate of the tertiary amine is used in an amount of 2 to 30% by weight based on the weight of the reaction mixture.

(4) The amount of water present in the reaction system is 25 to 60% by weight based on the weight of the reaction mixture.

(5) The amount of sulfolane present in the reaction system is 30 to 65% by weight based on the weight of the reaction mixture.

The synthesis of n-octadienol in step (i) of the process of this invention is usually carried out by introducing butadiene into an aqueous sulfolane solution containing palladium catalyst, phosphine of formula (I), tertiary amine and carbonate and/or bicarbonate ions. The reaction is carried out at a temperature of 10° to 50° C., preferably 20° to 120° C., and more preferably 50° to 110° C. Any gas-liquid contact type reactor known per se such as a stirring type reactor, an air-lift type reactor or the like may be used. The reaction may be conducted either batchwise or continuously, but a continuous process is more preferable from the viewpoint of commercial operation.

The desired product, n-octadienol, is subsequently separated by subjecting at least a part of the reaction mixture obtained in step (i) to solvent extraction in step (ii). The reaction mixture from step (i) generally forms a heterogeneous system. Accordingly, the upper layer which predominantly comprises n-octadienol may be separated before the lower layer is subjected to solvent extraction to extract n-octadienol present therein. The extractant should be selected upon consideration of various physical properties including boiling point, separability, extraction efficiency for n-octadienol, dissolution losses of sulfolane, palladium and phosphorine, and the like. The extractants which are satisfactory in these properties include saturated aliphatic hydrocarbons, monoolefinic hydrocarbons and alicyclic hydrocarbons. Illustrative of these solvents are n-butane, isobutane, butene, isobutene, n-pentane, n-hexane, cyclohexane, cyclohexene, n-heptane, methylcyclohexane, n-octane, isooctane, mixtures of butane, butene, isobutene, etc., contained in a $C_4$-fraction as a butadiene source, and the like. Particularly useful extractants are n-pentane, n-hexane, cyclohexane and methylcyclohexane. The extractant is generally used in an amount in the range of 0.5 to 15 volumés based on the volume of the reaction mixture. The extractant is usually added in step (ii), although a portion thereof may previously be added in step (i). In the solvent extraction of the reaction mixture obtained in step (i), n-octadienol can be efficiently extracted by maintaining the concentration of n-octadienol in the reaction mixture at 0.2 to 5.0 mole/liter, preferably 0.5 to 2.0 mole/liter. The extraction is generally carried out under an atmosphere of carbon dioxide or inert gas such as nitrogen or argon, using a extraction column conventionally employed in the commercial extraction procedure such as a perforate tower, a stirring type extractor, a RDC tower, a pulsating tower, etc.

A part or all of the extraction residue obtained in step (ii) which comprises an aqueous sulfolane solution containing the catalyst components is recycled to the synthesis of n-octadienol [step i)] and reused, if required, after the catalyst is partially re-activated.

The isolation of n-octadienol from the extract layer obtained in Step (ii) may be conducted in a conventional manner, and in general it is convenient to separate the extractant layer into unreacted starting material, by-products, extractant and n-octadienol by distillation. When the distillation procedure is employed, the bottoms of the distillation column may be at least partially recycled into the synthesis of n-octadienol in step (i). Prior to isolation of n-octadienol from the extract layer, the extract layer may be washed with water or an aqueous sulfolane solution, for example, to remove the trace amounts of the catalyst and phosphine contained therein. The n-octadienol prepared in accordance with the process of the present invention may be hydrogenated into n-octanol by any method known, although it may be used as a starting material for the preparation of chemicals as it is.

The following examples are given to illustrate the present invention, and they are not intended to limit the invention in any way.

EXAMPLE 1

A 200 ml-stainless steel electromagnetic stirring type autoclave equipped with a thermometer, a butadiene feed pump, a $CO_2$ inlet, solvent inlet, and a drain port was charged under nitrogen gas atmosphere with 44 mg (0.2 mmole) of palladium acetate, 60 ml of sulfolane solution containing 45 wt% water having 960 mg (2.4 mmole) of sodium diphenylphosphinobenzene-m-sulfonate.dihydrate

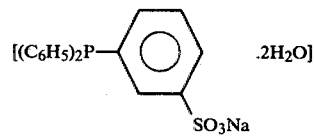

and 8 g of triethylamine.

The autoclave was then charged with 25 g of butadiene and 8.8 g of carbon dioxide (the concentration of water in the whole reaction mixture was 28 wt%). While the reaction mixture was stirred at 800 rpm, the temperature in the autoclave was elevated to 85° C. over a period of 30 minutes. The reaction was continued for another three hours at 85° C. After completion of the reaction, the temperature in the autoclave was cooled to room temperature and the pressure was allowed to decrease to atmospheric pressure. The whole reaction mixture taken out through the drain port consisted of two layers. A homogeneous solution obtained by adding tetrahydrofuran to the reaction mixture was analyzed by gas-chromatography: 20.8 g of 1-octa-2,7-dienol, 1.4 g of 3-octa-1,7-dienol, 1.2 g of octa-1,3,7-triene and 0.2 g of dioctadienyl ether were present in the solution.

EXAMPLE 2

Butadiene was reacted under the same conditions and using the same procedure as described in Example 1. After the reaction, the reaction mixture was taken out and mixed with 170 ml of cyclohexane with stirring. When the mixture was left to stand, it immediately separated into an upper colorless layer and a lower yellow layer. Analysis by gas chromatography showed that the upper layer contained 19.5 g of 1-octa-2,7-dienol, 1.3 g of 3-octa-1,7-dienol, 1.1 g of octa-1,3,7-triene, and 0.2 g of dioctadienyl ether. The palladium and phosphorus contents in the cyclohexane layer were determined by atomic absorption analysis and colorimetric analysis, respectively: the palladium atom content was 0.6 ppm and the phosphorus atom content was 1.4 ppm.

COMPARATIVE EXAMPLE 1

Butadiene was reacted under the same conditions and using the same procedure as described in Example 1 except that sodium diphenylphosphinobenzene-m-sulfonate was replaced by 2.4 mmole of triphenylphosphine. After the reaction, the reaction mixture was taken out and subsequently treated by extraction as described in Example 2 by adding 170 ml of cyclohexane to the mixture. Analysis by gas chromatography showed that the cyclohexane layer contained 7.2 g of 1-octa-2,7-dienol, 0.7 g of 3-octa-1,7-dienol and 0.4 g of octa-1,3,7-triene. The cyclohexane layer contained 82% of palladium based on the amount of palladium acetate employed, and 94% of triphenylphosphine based on the amount of triphenylphosphine employed.

COMPARATIVE EXAMPLE 2

Butadiene was reacted under the same conditions and using the same procedure as described in Example 1 except that the concentration of water in the sulfolane solution was 16.5 wt% instead of 45 wt% and that sodium diphenylphosphinobenzene-m-sulfonate was replaced by 2.4 mmole of triphenylphosphine. The reaction mixture was taken out through the drain port. The reaction mixture was homogeneous. About 2 ml of the reaction mixture was sampled and analyzed by gas-chromatography: the reaction products in the reaction mixture were 23.0 g of 1-octa-2,7-dienol, 1.9 g of 3-octa-1,7-dienol, 1.8 g of octa-1,3,7-triene and 0.2 g of dioctadienyl ether. When the reaction mixture was distilled in an oil bath at 130° C. under 100 mmHg, a large amount of carbon dioxide was evolved as the triethylamine bicarbonate decomposed, and then triethylamine, water and octatriene were recovered as distillates. When the distillation was continued at 130° C. under a pressure of 20 mmHg, a mixture (22 g) of 3-octa-1,7-dienol and 1-octa-2,7-dienol was obtained. The color of the distillation residue changed from yellow to brown and a precipitate of palladium metal was formed. When this distillation residue was subjected to the subsequent butadiene reaction, more palladium metal precipitated, and only 11 g of octadienols was produced. It was concluded from this result that distillation could not be used for separating n-octadienol from the reaction mixture.

EXAMPLES 3 to 6 and COMPARATIVE EXAMPLES 3 to 13

A reactor of the same type as used in Example 1 was charged with 22 mg (0.1 mmole) of palladium acetate, 2.0 mmole of monodentate phosphine, 60 ml of aqueous solution of organic solvent, and optionally 8 g of triethylamine. The reactor was then charged with 5 g of carbon dioxide and 12 g of butadiene. When triethylamine was used, the autoclave was charged with butadiene after carbon dioxide was supplied to convert triethylamine into a triethylamine bicarbonate. While the reaction mixture was stirred at 600 rpm, the temperature in the autoclave was elevated to 75° C. over a period of 30 minutes. The reaction was continued for another three hours at 75° C. After the reaction, tetrahydrofuran was added to the reaction mixture as described in Example 1 to provide a homogeneous solution which was then subjected to gas chromatographic analysis. Table 1 shows the effect of the use of different organic solvents and different monodentate phosphines and of the addition of triethylamine on catalytic activity

TABLE 1

|  | Organic solvent[1] | Monodentate phosphine | Triethylamine (mmole) | Octadienol Yield (mmole) | 1/3 (molar ratio)[2] | Selectivity (%)[3] |
|---|---|---|---|---|---|---|
| Ex. 3 | Sulfolane | 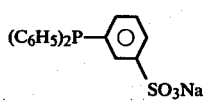 | 64 | 93 | 94/6 | 91 |
| Ex. 4 | Sulfolane | 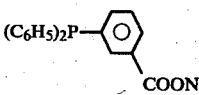 | 64 | 90 | 93/7 | 90 |

TABLE 1-continued

| | Organic solvent[1] | Monodentate phosphine | Triethyl-amine (mmole) | Octadienol Yield (mmole) | Octadienol 1/3 (molar ratio)[2] | Selectivity (%)[3] |
|---|---|---|---|---|---|---|
| Ex. 5 | Sulfolane | C$_6$H$_5$—P+(—⟨O⟩—SO$_3$Na)$_2$ | 64 | 93 | 94/6 | 91 |
| Ex. 6 | Sulfolane | P+[⟨O⟩—CH$_2$N(CH$_3$)$_2$]$_3$ | 64 | 91 | 92/8 | 90 |
| Comp. Ex. 3 | Sulfolane | P+[⟨O⟩—CH$_2$N(CH$_3$)$_2$]$_3$ | 0 | 21 | 92/8 | 91 |
| 4 | t-Butanol | P+[⟨O⟩—CH$_2$N(CH$_3$)$_2$]$_3$ | 64 | 18 | 71/29 | 67 |
| 5 | Acetone | P+[⟨O⟩—CH$_2$N(CH$_3$)$_2$]$_3$ | 64 | 12 | 53/47 | 49 |
| 6 | Acetone | P+[⟨O⟩—CH$_2$N(CH$_3$)$_2$]$_3$ | 0 | 8 | 61/39 | 54 |
| 7 | Dioxane | P+[⟨O⟩—CH$_2$N(CH$_3$)$_2$]$_3$ | 64 | 11 | 48/52 | 44 |
| 8 | N-methyl-pyrrolidone | P+[⟨O⟩—CH$_2$N(CH$_3$)$_2$]$_3$ | 64 | 23 | 70/30 | 61 |
| 9 | Aceto-nitrile | P+[⟨O⟩—CH$_2$N(CH$_3$)$_2$]$_3$ | 64 | 30 | 81/19 | 60 |
| Comp. Ex. 10 | Aceto-nitrile | P+[⟨O⟩—CH$_2$N(CH$_3$)$_2$]$_3$ | 0 | 5 | 89/11 | 44 |
| 11 | Dimethyl sulfoxide | P+[⟨O⟩—CH$_2$N(CH$_3$)$_2$]$_3$ | 64 | 8 | 72/28 | 65 |
| 12 | N-methyl-morpholine | (C$_6$H$_5$)$_2$P—⟨O⟩—SO$_3$Na | 0 | 6 | 68/32 | 62 |
| 13 | N,N-di-methyl-formamide | (C$_6$H$_5$)$_2$P—⟨O⟩—SO$_3$Na | 64 | 9 | 82/18 | 67 |

[1]The content of water in each aqueous solution of organic solvent was 45 wt % (equivalent to 33 wt % based on the whole reaction mixture).
[2]The molar ratio of 1-octa-2,7-dienol to 3-octa-1,7-dienol produced.
[3]1-Octa-2,7-dienol (mmole)/whole reaction product (mole) × 100.

Table 1 shows that the combination of sulfolane and triethylamine afforded satisfactory results with respect to reaction rate and reaction selectivity.

EXAMPLES 7 to 12 and COMPARATIVE EXAMPLES 14 to 17

A reactor of the same type as used in Example 1 was charged with 22 mg (0.1 mmole) of palladium acetate, 480 mg (1.2 mmole) of sodium diphenylphosphinobenzene-m-sulfonate.dihydrate, 60 ml of sulfolane solution of various water concentrations, and 6.5 g of tertiary amine. The reactor was then charged with 5 g of carbon dioxide and 25 g of butadiene. While the reaction mixture was stirred at 800 rpm, the temperature in the autoclave was elevated to 75° C. over a period of 30 minutes. The reaction was continued for another three hours at 75° C. with stirring. After the reaction, tetrahydrofuran was added to the reaction mixture to provide a homogeneous solution which was then subjected to gas chromatographic analysis. Table 2 shows the effect of different water concentrations in the sulfolane solution and the effect of the use of a given tertiary amine on the catalytic activity.

TABLE 2

| Ex. | Water conc. (wt %)[1] | Tertiary amine | Octadienol Yield (mmole) | 1/3 (molar ratio) |
|---|---|---|---|---|
| Ex. 3 | 45 | Triethylamine | 93 | 94/6 |
| 7 | 45 | Tri-n-propylamine | 86 | 93/7 |
| 8 | 45 | N,N'—dimethylpiperazine | 70 | 91/9 |
| 9 | 45 | N—methylmorpholine | 77 | 95/5 |
| 10 | 45 | N,N,N',N'—tetramethyl-1,3-butanediamine | 65 | 91/9 |
| 11 | 35 | Triethylamine | 108 | 92/8 |
| 12 | 55 | Triethylamine | 75 | 94/6 |
| Comp. Ex. 14 | 90 | Triethylamine | 1 | 81/19 |
| 15 | 45 | Pyridine | 10 | 90/10 |
| 16 | 45 | α,α'-dipyridyl | 0 | — |
| 17 | 45 | N,N,N',N'—tetramethyl-1,2-ethanediamine | 2 | 58/42 |

[1]Water/water + sulfolane (wt %)

COMPARATIVE EXAMPLE 18

Butadiene was reacted under the same conditions and using the same procedure as described in Example 1 except that the concentration of water in the aqueous sulfolane solution was 16.5 wt% instead of 45 wt%. The reaction mixture was homogeneous. Analysis by gas chromatography showed that the reaction products in the reaction mixture were 23.4 g of 1-octa-2,7-dienol, 1.5 g of 3-octa-1,7-dienol, 1.7 g of octa-1,3,7-triene and 0.2 g of dioctadienyl ether. Only 21% of 1-octa-2,7-dienol could be extracted from the reaction mixture after extraction with 170 ml of cyclohexane.

The results of Comparative Examples 14 and 18 show that the water concentration in the reaction mixture must be controlled in a suitable range because it is a predominant factor that governs the reaction rate and the efficiency of extraction of the desired components in the extraction step.

EXAMPLES 13 to 17

A reactor of the same type as used in Exmaple 1 was charged with 22 mg (0.1 mmole) of palladium acetate, various concentrations of sodium diphenylphosphino-benzene-m-sulfonate.dihydrate, various concentrations of triethylamine bicarbonate, and 60 ml of an aqueous sulfolane solution containing water whose concentration was 33 wt% based on the whole reaction mixture. After supplying carbon dioxide to provide a pressure of 8 kg/cm² G, the autoclave was charged with 15 g of butadiene. While the reaction mixture was stirred at 800 rpm, the autoclave was heated at 80° C. for 3 hours. After the reaction, tetrahydrofuran was added to the reaction mixture to provide a homogeneous solution which was then subjected to gas chromatographic analysis. Table 3 shows the effect the concentration of triethylamine bicarbonate and the concentration of sodium diphenylphosphinobenzene-m-sulfonate.dihydrate (P/Pd atomic ratio), has on the catalyst activity.

TABLE 3

| Ex. No. | Conc. of tri- ethyl- amine bicar- bonate (wt %)[1] | Amt. of (C6H5)2P——SO3Na added (mmole) | P/Pd (atm. ratio) | Octadienol Yield (mmole) | 1/3 |
|---|---|---|---|---|---|
| 13 | 11 | 0.8 | 8 | 73 | 94/6 |
| 14 | 11 | 1.5 | 15 | 77 | 94/6 |
| 15 | 11 | 3.5 | 35 | 72 | 93/7 |
| 16 | 15 | 1.5 | 15 | 91 | 94/6 |
| 17 | 6 | 1.5 | 15 | 59 | 93/7 |

[1]Concentration of triethylamine bicarbonate based on the whole reaction mixture

Table 3 shows that when sodium diphenylphosphino-benzene-m-sulfonate is used in an excess amount with respect to palladium in combination with triethylamine bicarbonate, little change occurs in the reaction rate and in the selectivity for 1-octa-2,7-dienol. The data also show that the addition of a large excess of triethylamine bicarbonate increases rather than decreases the reaction rate.

EXAMPLE 18

The drain port of a reactor of the same type as used in Example 1 was connected to a 1-liter pressure-resistant glass autoclave (extractor) equipped with a stirrer, a N₂ inlet, solvent inlet and a drain port. The reactor was charged under nitrogen gas atmosphere with 44 mg (0.2 mmole) of palladium acetate, 60 ml of sulfolane solution containing 45 wt% water which had dissolved therein 1200 mg (3.0 mmole) of sodium diphenylphosphinobenzene-m-sulfonate.dihydrate and 48.6 mg (0.2 mmole) of (C₆H₅)₂PCH₂N(CH₃)₂, and 8 g of triethylamine. The reactor was then charged with 25 g of butadiene and 8 g of carbon dioxide. While the reaction mixture was stirred at 800 rpm, the temperature in the reactor was elevated to 80° C. over a period of 30 minutes. The reaction was continued for another three hours at 80° C. The stirring was stopped and the temperature in the reactor was cooled to room temperature and the reaction mixture was transferred into the glass autoclave (extractor) with the aid of residual pressure. After the pressure in the extractor was allowed to decrease to atmospheric pressure, 200 ml of cyclohexane and 2 g of water were added to the reaction mixture under nitrogen gas atmosphere, and the resulting mixture was stirred vigorously for about 5 minutes. When the stirring was stopped, the mixture immediately separated into an upper colorless layer and a lower yellow layer. The upper cyclohexane layer was recovered under nitrogen atmosphere and subjected to gas chromatographic analysis. The lower layer (catalyst solution) was mixed with 0.5 g of triethylamine and the mixture was transferred to the autoclave with the aid of the nitrogen gas pressure. After supplying carbon dioxide to a pressure of 7 kg/cm² G, the autoclave was charged with 25 g of butadiene. While the reaction mixture was stirred at 800 rpm, the autoclave was heated to 80° C. over a period of 30 minutes, and the reaction was continued for another three hours at 80° C. The stirring was stopped and the temperature in the reactor was cooled to room temperature and the reaction mixture was transferred to the glass autoclave with the aid of pressure. After the pressure in the autoclave was allowed to degas to atmospheric pressure, 200 ml of cyclohexane and 2 g of water were added to the reaction mixture under nitrogen gas atmosphere, and the extraction residue was again mixed with 0.5 g of triethylamine and the mixture was transferred to the autoclave under pressure. Repeating these procedures, the reaction of butadiene and the extraction with cyclohexane were performed six times. Table 4 shows the results of analysis of the cyclohexane layer obtained in each run and from extraction.

TABLE 4

| Run No. | Yield (mmole) | | | |
|---|---|---|---|---|
| | Octadienol | (1/3) | Octa-1,3,7-triene | Dioctadienyl ether |
| 1 | 120 | (93/7) | 2.8 | 1.2 |
| 2 | 145 | (92/8) | 3.1 | 1.6 |
| 3 | 133 | (92/8) | 2.5 | 1.5 |
| 4 | 134 | (92/8) | 2.4 | 1.5 |
| 5 | 134 | (92/8) | 2.4 | 1.5 |
| 6 | 137 | (92/8) | 2.5 | 1.5 |

Table 4 demonstrates that catalytic activity did not decrease upon repeated reaction and extraction.

EXAMPLES 19 and 20 and COMPARATIVE EXAMPLE 19

The effects of differences in amounts of monodentate phosphine and differences in addition of bidentate phosphine on the life of catalyst were examined by performing repeated reaction in a reactor of the same type as used in Example 18 and using the same procedure as employed in Example 18. The reactor was first charged with solution containing 70 mg (0.31 mmole) of palladium acetate, 58 g of sulfolane, 48 g of water and 14 g of triethylamine bicarbonate. The reactor was then charged with 10 g of butadiene under a $CO_2$ pressure of 8 kg/cm$^2$G. While the reaction mixture was stirred at 800 rpm, the temperature in the reactor was held at 80° C. for one hour. After the reaction, the reaction mixture was subjected to extraction twice using 50 ml of n-hexane. This procedure was repeated ten times as described in Example 18. Table 5 shows the amount of octadienol in the n-hexane layer obtained in the 2nd, 5th, 7th and 10th runs.

TABLE 5

| | Sodium diphenyl-phosphinobenzene-m-sulfonate/Pd (molar ratio) | Molar ratio of bidentate phosphine: $(C_6H_5)_2P(CH_2)_4P$ with $C_6H_5$ / $SO_3Na$ to Pd | Yield of octadienol (mmole) | | | |
|---|---|---|---|---|---|---|
| | | | 2nd | 5th | 7th | 10th |
| Ex. 19 | 20 | 0 | 72 | 74 | 72 | 72 |
| Comp. Ex. 19 | 5 | 0 | 77 | 61 | 38 | |
| Ex. 20 | 6 | 1 | 64 | 64 | 63 | 65 |

It can be observed from Table 5 that the monodentate phosphine added in great excess with respect to palladium maintained the catalytic activity whereas about 5 moles of the monodentate phosphine per mole of palladium was not able to prevent deactivation of the catalyst. When the bidentate phosphine was added in an equi-molar amount with respect to palladium in combination with the monodentate phosphine, the catalytic activity was maintained almost the same throughout the ten runs. The reaction mixture obtained in Example 20 apparently contained no phosphine oxide derived from the monodentate phosphine.

EXAMPLE 21

A test on catalytic activity was conducted by repeating the cycles of reaction, extraction and washing 32 times using apparatuses described below.

Reactor

The reactor was a 300-ml stainless steel autoclave equipped with a thermometer, a stirrer, butadiene feed pump, a $CO_2$ inlet, solvent inlet, and a drain port.

Extractor

The extractor was a 800-ml pressure-resistant glass autoclave equipped with a thermometer, a stirrer, gas inlet, n-hexane inlet, and a port through which the extract was transferred to the following water washing apparatus with the aid of pressure. The extractor was directly connected to the reactor.

Water Washing Apparatus

The apparatus was a 300-ml flask equipped with a stirrer, gas inlet, extract inlet and extract outlet. The water washing apparatus was directly connected with the reactor and extractor by a pipe.

Testing Method

The reactor described above was charged with 58 g of sulfolane, 48 g of distilled water, 8.8 g of triethylamine (corresponding to 14.2 g of triethylamine bicarbonate), 70 mg of palladium acetate (corresponding to 2.9 mmole/liter of the whole charge), 3.2 g of sodium diphenylphosphinobenzene-m-sulfonate.dihydrate and 120 mg of

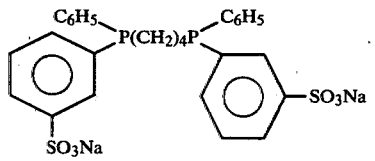

After purging the reactor with carbon dioxide thoroughly, the temperature in the reactor was elevated to 80° C. with stirring, and carbon dioxide was supplied until the pressure in the autoclave reached 8 kg/cm$^2$G.

While the reaction mixture was stirred at 600 rpm, the reactor was held at 80° C. for 60 minutes with liquid butadiene being supplied continuously at a rate of 15 ml/hr. Sixty minutes later, the supply of butadiene was stopped, and the reaction mixture with cooling was sent to the extractor under pressure of carbon dioxide. After the extractor was pressured with carbon dioxide to 3 kg/cm²G, 50 ml of n-hexane was added to the reaction mixture at 40° C. The reaction product was extracted with n-hexane with stirring at 600 rpm for 15 minutes. After stirring, the mixture was left to stand for about 20 minutes. The upper layer (n-hexane layer) was transferred with the aid of carbon dioxide pressure to the water washing apparatus, whereupon the residue was again extracted with 50 ml of n-hexane under the same conditions as employed above. The resulting hexane layer was sent to the water washing apparatus under pressure. The residue layer containing the catalyst was sent back to the reactor under pressure of carbon dioxide. One milliliter of water was added to the n-hexane layer, and the mixture was stirred at 800 rpm for 15 minutes at room temperature under a $CO_2$ atmosphere. After letting the mixture stand for a while, the n-hexane layer was taken out. The aqueous layer was finally combined with the corresponding amounts of sulfolane, triethylamine and water dissolved in the n-hexane layer, and sent to the reactor under pressure. The above procedure was repeated 32 times using the same catalyst solution. No additional palladium catalyst and organic phosphorus compound was supplied during the entire period of the testing. The contents of reaction product and sulfolane in the n-hexane layer were analyzed by gas-chromatography, the triethylamine content by titration method, water content by the Karl Fisher method, and the palladium atom and phosphorus atom contents by atomic absorption analysis and colorimetric analysis, respectively. Table 6 shows how the yield of octadienol and the amounts of palladium catalyst and organic phosphorus compound dissolved in the n-hexane layer changed with the number of cycles of reaction, extraction, and washing. Table 6 shows that the activity of the catalyst according to this invention was maintained for an extended period of time.

TABLE 6

| No. of cycles | Octadienol[1] Yield (mmole) | 1/3 | Conc. (ppm) of catalyst components in n-hexane layer Pd | P |
|---|---|---|---|---|
| 5 | 71 | 94/6 | 0.20 | 1.2 |
| 10 | 71 | 94/6 | 0.18 | 1.3 |
| 15 | 70 | 94/6 | 0.18 | 1.3 |
| 20 | 71 | 95/5 | 0.20 | 1.4 |
| 25 | 70 | 94/6 | 0.20 | 1.3 |
| 32 | 70 | 94/6 | 0.21 | 1.4 |

[1]The yields of octa-1,3,7-triene and dioctadienyl ether were 2.4–2.6 millimoles and 0.4–0.6 millimoles, respectively, which did not change with the increase in the number of cycles.

What we claim is:

1. A process for preparing n-octadienol, comprising the steps of:
   (i) reacting at a temperature of 10° C. to 150° C. butadiene with water in an aqueous sulfolane solution having a water/sulfolane weight ratio in the range of 20/80 to 70/30 and containing carbonate ions, bicarbonate ions or mixtures thereof, in the presence of (A) palladium or a palladium compound, (B) a monodentate phosphine of the formula:

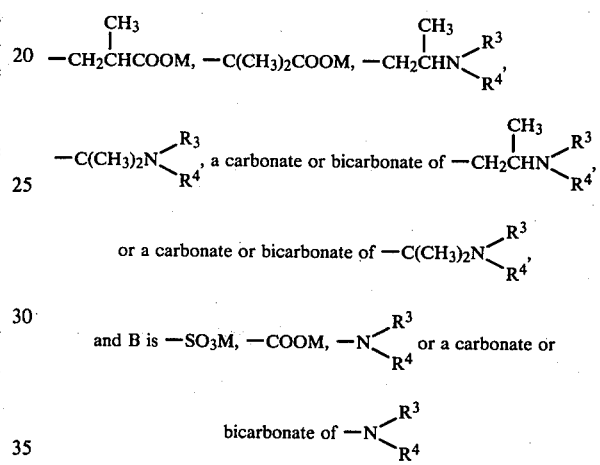

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy, or halogen; n is 0 or 1, x is 0, 1 or 2, and y and z are each 0, 1, 2 or 3, with the proviso that y and z are not concurrently equal to 0 and that $x+y+z=3$; A is $$-CH_2CHCOOM, -C(CH_3)_2COOM, -CH_2CHN\begin{matrix}R^3\\R^4\end{matrix},$$
$$\quad | \\ \quad CH_3$$

$-C(CH_3)_2N\begin{matrix}R^3\\R^4\end{matrix}$, a carbonate or bicarbonate of $-CH_2CHN\begin{matrix}R^3\\R^4\end{matrix}$
$\qquad\qquad\qquad\qquad\qquad\qquad\qquad\qquad | \\ \qquad\qquad\qquad\qquad\qquad\qquad\qquad\qquad CH_3$ or a carbonate or bicarbonate of $-C(CH_3)_2N\begin{matrix}R^3\\R^4\end{matrix}$, and B is $-SO_3M$, $-COOM$, $-N\begin{matrix}R^3\\R^4\end{matrix}$ or a carbonate or bicarbonate of $-N\begin{matrix}R^3\\R^4\end{matrix}$ wherein $R^3$ and $R^4$ are each methyl, ethyl or n-propyl and M is an alkali metal in an amount of at least 6 moles per gram atom of said palladium; and (C) a monodentate tertiary amine having a basicity constant (pKa) of at least 7 in an amount of 1 to 50% by volume based on the sulfolane to form n-octadienol;
   (ii) extracting at least part of the reaction mixture obtained in step (i) with a saturated aliphatic hydrocarbon, a monoolefinic hydrocarbon or an alicyclic hydrocarbon; and
   (iii) recycling at least part of the extraction residue obtained in step (ii) which contains the catalyst components to step (i).

2. The process of claim 1 wherein the sulfolane solution has a water/sulfolane weight ratio in the range of 25/75 to 60/40.

3. The process of claim 1 wherein the concentration of the palladium or palladium compound is between 0.1 and 50 milligram atom as palladium atom per liter of the aqueous sulfolane solution.

4. The process of claim 1 wherein the monodentate phosphine of formula (I) is added in an amount of 10 to 50 moles per gram atom of the palladium.

5. The process of claim 1 wherein said tertiary amine is selected from the group consisting of tri(lower) alkylamine, aminoalcohols, N,N-dimethyl-2-methoxyethylamine, N,N-dimethyl-3-ethoxypropylamine, N-methylpyrrolidine, N,methylpiperidine, N,-methylmorpholine, N,N-dimethylpiperazine and N,N,N,N-tetramethyl-1,3-butanediamine.

6. The process of claim 1 wherein the carbonate and/or bicarbonate ion is derived from carbon dioxide, sodium bicarbonate or formic acid.

7. The process of claim 1 wherein a Bidentate phosphine of the formula:

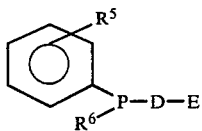
(II)

wherein $R^5$ is hydrogen, methyl, halogen, cyano, methoxy, nitro,

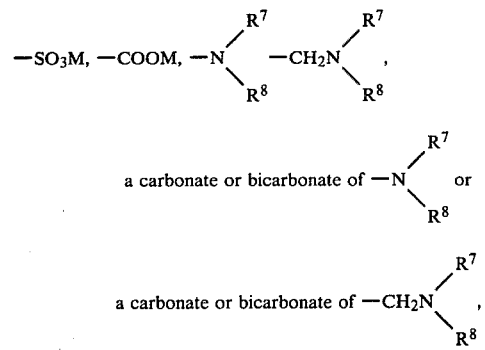

wherein $R^7$ and $R^8$ are each methyl, ethyl or n-propyl, and M is an alkali metal,
$R^6$ is a hydrocarbon group having 1 to 8 carbon atoms;
D is $-(CH_2)_n-$, wherein n is an integer of 1 to 4,

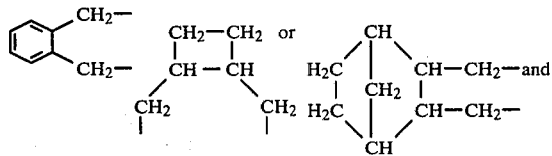

E is 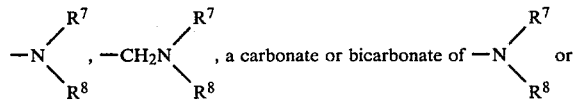, wherein $R^9$ is $-SO_3M$, $-COOM$,

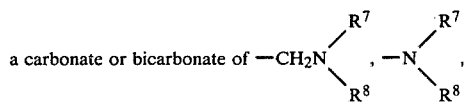

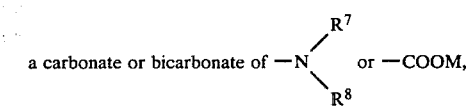

is added in an amount of 0.3 to 3 moles per gram atom of the palladium to said reaction.

8. The process of claim 1, wherein the reaction in step (i) is carried out with butadiene being introduced continuously or intermittently into the reaction system so as to maintain the concentration of butadiene in the reaction system at 0.1 to 10% by weight.

9. The process of claim 1, wherein said phosphine is that of formula (I) wherein $R^1$ is an aromatic hydrocarbon; n is 0 or 1, x is 0, 1 or 2, y is 0 or 1 and z is 0, 1, 2 or 3, with the proviso that y and z are not concurrently equal to 0 and that $x+y+z=3$;

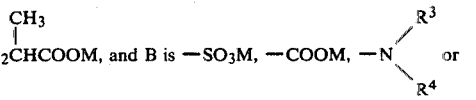

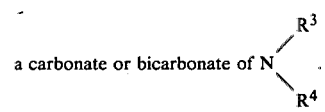

10. The process of claim 1, wherein said extractant in step (ii) is a saturated aliphatic hydrocarbon selected from the group consisting of n-pentane and n-hexane or an alicyclic hydrocarbon selected from the group consisting of cyclohexane and methylcyclohexane.

11. The process of claim 1, wherein the concentration of n-octadienol in the reaction mixture in step (ii) is in the range of 0.5 to 2 moles/liter.

12. A process for preparing n-octadienol, comprising the steps of:
(i) reacting at a temperature of 10° C. to 150° C. butadiene with water in a solution containing water, a carbonate and/or bicarbonate of a monodentate tertiary amine having a basicity constant (pKa) of at least 7 and sulfolane in amounts of 25 to 60%, 2 to 30% and 30 to 65%, respectively, by weight based on the resulting reaction mixture, in the presence of (A) palladium or a palladium compound in an amount of 0.5 to 20 milligram atom as palladium atom per liter of the sulfolane solution and (B) a monodentate phosphine of the formula:

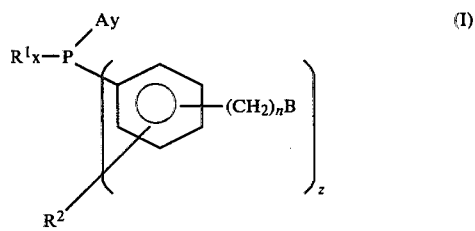
(I)

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy, or halogen; n is 0 or 1, x is 0, 1 or 2, and y and z are each 0, 1, 2 or 3, with the proviso that y and z are not concurrently equal to 0 and that $x+y+z=3$;

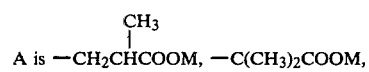

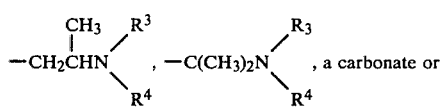

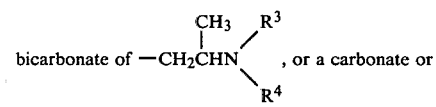

bicarbonate of 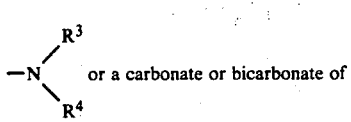, and B is —SO₃M, —COOM,

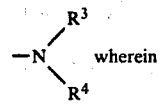 or a carbonate or bicarbonate of

—N(R³)(R⁴) wherein

R³ and R⁴ are each methyl, ethyl or n-propyl and M is an alkali metal in an amount of at least 10 to 50 moles per gram atom of said palladium to form n-octadienol;

(ii) extracting at least part of the reaction mixture obtained in step (i) with a saturated aliphatic hydrocarbon, a monoolefinic hydrocarbon or an alicyclic hydrocarbon; and (iii) recycling at least part of the extraction residue obtained in step (ii) which contains the catalyst components to step (i).

13. The process of claim 12, wherein said monodentate tertiary amine is selected from the group consisting of tri(lower) alkylamine, aminoalcohols, N,N-dimethyl-2-methoxy-ethylamine, N,N-dimethyl-3-ethoxypropylamine, N-methylpyrrolidine, N,methylpiperidine, N-methylmorpholine, N,N-dimethylpiperazine and N,N,N,N-tetramethyl-1,3-butanediamine.

14. The process of claim 12, wherein the reaction in step (i) is carried out with butadiene being introduced continuously or intermittently into the reaction system so as to maintain the concentration of butadiene in the reaction system at 0.1 to 10% by weight.

15. The process of claim 12, wherein said monodentate phosphine is that of formula (I) in which R¹ is an aromatic hydrocarbon group; n is 0 or 1, x is 0, 1 or 2, y is 0 or 1 and z is 0, 1, 2 or 3, with the proviso that y and z are not concurrently equal to 0 and that x+y+z=3;

A is —CH₂CH(CH₃)COOM and B is —SO₃M, —COOM, —N(R³)(R⁴) or a carbonate or bicarbonate of —N(R³)(R⁴)

16. The process of claim 12, wherein the monodentate phosphine of formula (I) is selected from the group consisting of

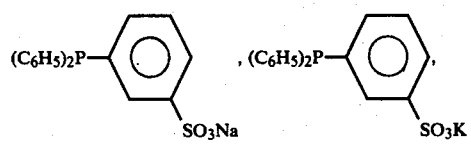

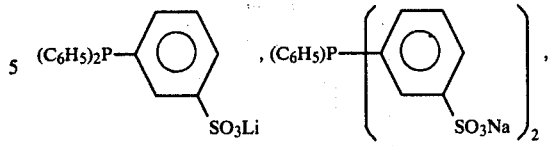

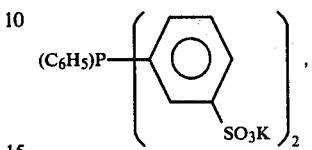

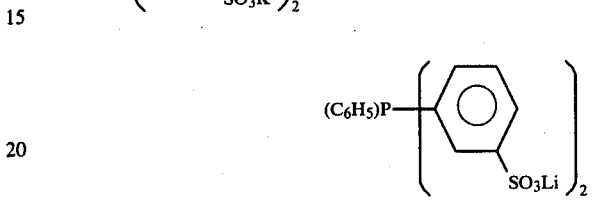

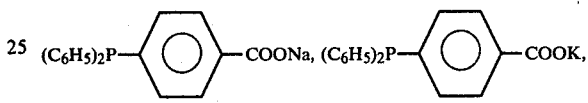

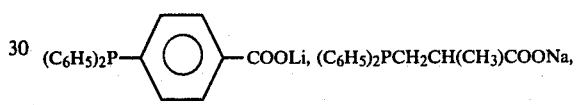

(C₆H₅)₂PCH₂CH(CH₃)COOK and (C₆H₅)₂PCH₂CH(CH₃)COOLi.

17. The process of claim 12 wherein a bidentate phosphine of the formula:

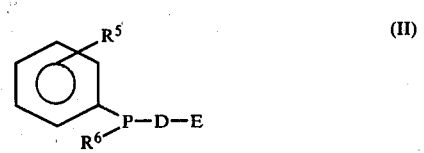

(II)

wherein R⁵ is hydrogen, methyl, halogen, cyano, methoxy, nitro, —SO₃M, —COOM, 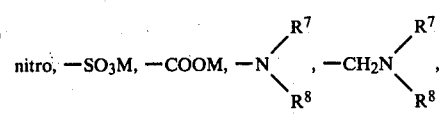

a carbonate or bicarbonate of —N(R⁷)(R⁸) or a carbonate or bicarbonate of —CH₂N(R⁷)(R⁸), wherein R⁷ and R⁸ are each methyl, ethyl or n-propyl and M is an alkali metal,
R⁶ is a hydrocarbon group having 1 to 8 carbon atoms;
D is —(CH₂)ₙ—, wherein n is an integer of 1 to 4, -continued

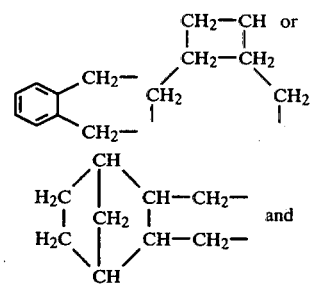

and

E is 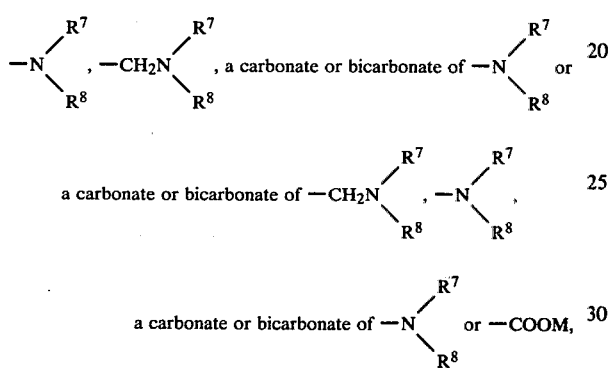, wherein $R^9$ is $-SO_3M$, $-COOM$, $-N\begin{smallmatrix}R^7\\R^8\end{smallmatrix}$, $-CH_2N\begin{smallmatrix}R^7\\R^8\end{smallmatrix}$, a carbonate or bicarbonate of $-N\begin{smallmatrix}R^7\\R^8\end{smallmatrix}$ or a carbonate or bicarbonate of $-CH_2N\begin{smallmatrix}R^7\\R^8\end{smallmatrix}$, $-N\begin{smallmatrix}R^7\\R^8\end{smallmatrix}$, a carbonate or bicarbonate of $-N\begin{smallmatrix}R^7\\R^8\end{smallmatrix}$ or $-COOM$, is added to said reaction in an amount of 0.3 to 3 moles per gram atom of the palladium.

18. The process of claim 12, wherein said extractant in step (ii) is a saturated aliphatic hydrocarbon selected from the group consisting of n-pentane and n-hexane or an alicyclic hydrocarbon selected from the group consisting of cyclohexane and methylcyclohexane.

19. The process of claim 12, wherein the concentration of n-octadienol in the reaction mixture from step (i) is 0.5 to 2 moles/liter.

20. A process for preparing n-octadienol, comprising the steps of:
(i) reacting butadiene with water in an aqueous sulfolane solution having a water/sulfolane weight ratio in the range of 20/80 to 70/30 and containing carbonate ions, bicarbonate ions or mixtures thereof in the presence of (A) palladium or a palladium compound, (B) a monodentate phosphine of the formula:

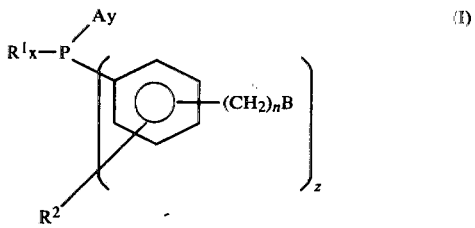 (I)

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that $x+y+z=3$; A is $-CH_2\overset{CH_3}{\underset{}{C}}HCOOM$, $-C(CH_3)_2COOM$, $-CH_2CHN\begin{smallmatrix}CH_3\\|\\R^3\\R^4\end{smallmatrix}$,

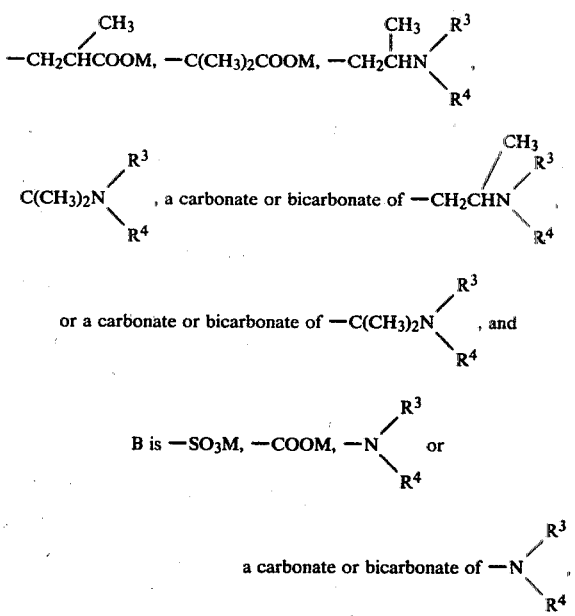

wherein $R^3$ and $R^4$ are each methyl, ethyl or n-propyl and M is an alkali metal in an amount of at least 6 moles per gram atom of said palladium and (C) a monodentate tertiary amine having a basicity constant (pKa) of at least 7 in an amount of 1 to 50% by volume based on the sulfolane to form n-octadienol.

21. The process of claim 1, wherein the reaction temperature is 50° C. to 110° C.

22. The process of claim 12, wherein the reaction temperature is 50° C. to 110° C.

* * * * *